(12) United States Patent
Colloca et al.

(10) Patent No.: US 11,643,666 B2
(45) Date of Patent: May 9, 2023

(54) EUKARYOTIC CELL LINE

(71) Applicant: NOUSCOM AG, Basel (CH)

(72) Inventors: Stefano Colloca, Rome (IT); Alfredo Nicosia, Naples (IT)

(73) Assignee: NOUSCOM AG, Basel (CH)

( * ) Notice: Subject to any disclaimer, the term of this patent is extended or adjusted under 35 U.S.C. 154(b) by 389 days.

(21) Appl. No.: 16/759,632

(22) PCT Filed: Oct. 25, 2018

(86) PCT No.: PCT/EP2018/079341
§ 371 (c)(1),
(2) Date: Apr. 27, 2020

(87) PCT Pub. No.: WO2019/081673
PCT Pub. Date: May 2, 2019

(65) Prior Publication Data
US 2020/0308601 A1    Oct. 1, 2020

(30) Foreign Application Priority Data
Oct. 25, 2017 (EP) ..................................... 17198339

(51) Int. Cl.
| | | |
|---|---|---|
| C12N 15/86 | (2006.01) | |
| C12N 7/00 | (2006.01) | |
| C12N 5/073 | (2010.01) | |
| C12N 5/10 | (2006.01) | |

(52) U.S. Cl.
CPC ........... C12N 15/86 (2013.01); C12N 5/0603 (2013.01); C12N 5/10 (2013.01); C12N 7/00 (2013.01); *C12N 2710/10322* (2013.01); *C12N 2710/10343* (2013.01); *C12N 2710/10352* (2013.01); *C12N 2830/006* (2013.01)

(58) Field of Classification Search
CPC ........ C12N 15/86; C12N 5/0603; C12N 5/10; C12N 7/00; C12N 2710/10322; C12N 2710/10343; C12N 2710/10352; C12N 2830/006
See application file for complete search history.

(56) References Cited

U.S. PATENT DOCUMENTS

2009/0130763 A1   5/2009   Miwa

FOREIGN PATENT DOCUMENTS

| GB | 2 540 786 | 2/2017 |
| WO | 2006/085590 | 8/2006 |
| WO | WO 2007/032555 | 3/2007 |
| WO | 2007/073513 | 6/2007 |
| WO | WO-2017152042 A2 * | 9/2017 ............. A61K 39/00 |
| WO | 2018/213353 | 11/2018 |

OTHER PUBLICATIONS

Chen et al. A Comparison of Exogenous Promoter Activity at the ROSA26 Locus Using a PhiC31 Integrase Mediated Cassette Exchange Approach in Mouse ES Cells. PLoS ONE. 2011, 6(8): e23376. (Year: 2011).*
Luo et al. Stable Enhanced Green Fluorescent Protein Expression After Differentiation and Transplantation of Reporter Human Induced Pluripotent Stem Cells Generated by AAVS1 Transcription Activator-Like Effector Nucleases. Stem Cells Translational Medicine, 2014; 3:821-835. (Year: 2014).*
Kosuga et al. Strong, Long-Term Transgene Expression in Rat Liver Using Chicken (5-Actin Promoter Associated With Cytomegalovirus Immediate-Early Enhancer (CAG Promoter). Cell Transplantation, 2000, 9: 675-680, (Year: 2000).*
Kantner et al. ETV6/RUNX1 Induces Reactive Oxygen Species and Drives the Accumulation of DNA Damage in B Cells. Neoplasia. 2013, 15, 1292-1300. (Year: 2013).*
The International Preliminary Report on Patentability (IPRP) for PCT/EP2018/079341 dated Jul. 26, 2019, pp. 1-15.
The International Search Report (ISR) with Written Opinion for PCT/EP2018/079341 dated Nov. 12, 2018, pp. 1-11.
H J Stewart et al. "Development of inducible EIAV-based lentiviral vector packaging and producer cell lines", Gene Therapy, vol. 16, No. 6, Mar. 5, 2009 (Mar. 5, 2009), pp. 805-814.
L. Sun et al. "Cyclic GMP-AMP Synthase Is a Cytosolic DNA Sensor That Activates the Type I Interferon Pathway", Science, vol. 339, No. 6121, Feb. 15, 2013 (Feb. 15, 2013), pp. 786-791.
Gaetano Zafarana et al. "Specific Knockdown of OCT4 in Human Embryonic Stem Cells by Inducible Short Hairpin RNA Interference", Stem Cells., vol. 27, No. 4, Apr. 1, 2009 (Apr. 1, 2009), pp. 776-782.
Hejnar J et al. :Inhibition of the rous sarcoma virus long terminal repeat-driven transcription by in vitro methylation: different sensitivity in permissive chicken cells versus mammalian cells Virology. Mar. 1, 1999;255(1):171-81. (ABSTRACT).
Kaufman Wl et al. "Homogeneity and persistence of transgene expression by omitting antibiotic selection in cell line isolation" Nucleic Acids Res. Oct. 2008;36(17):e111. doi: 10.1093/nar/gkn508. Epub Aug. 5, 2008.(ABSTRACT).
Robert-Richard E. et al. "Murine retroviral but not human cellular promoters induce in vivo erythroid-specific deregulation that can be partially prevented by insulators" Mol Ther. Jan. 2007;15(1):173-82.(ABSTRACT).
Moritz, et al., (Nov. 2015) "CMV promotor mutants with a reduced propensity to productivity loss in CHO cells," Scientific Reports, 5:16952.

* cited by examiner

*Primary Examiner* — Arthur S Leonard
*Assistant Examiner* — Jianjian Zhu
(74) *Attorney, Agent, or Firm* — McDonnell Boehnen Hulbert & Berghoff LLP

(57) ABSTRACT

The present invention relates to a cell line, use of the cell line and a method for producing infectious viral particles using said cell line.

Figure 1:
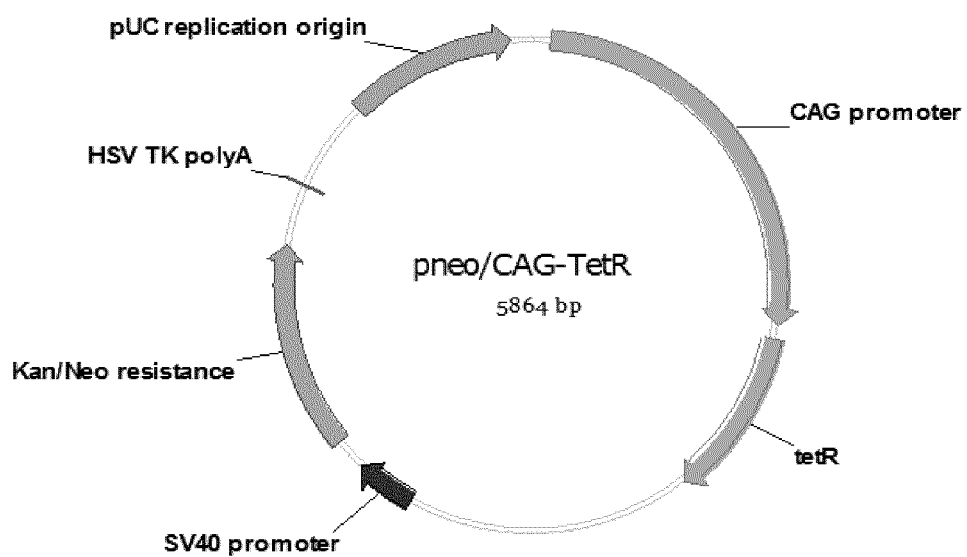

13 Claims, 11 Drawing Sheets
Specification includes a Sequence Listing.

A

B

A

B

Adenoviral vector carrying a HCMV promotor with TetO

Diagram of the expression cassette including TetO sequences

SEQUENCE LISTING

<160> NUMBER OF SEQ ID NOS: 3

<210> SEQ ID NO 1
<211> LENGTH: 4344
<212> TYPE: DNA
<213> ORGANISM: Homo sapiens

<400> SEQUENCE: 1

```
catcatcaat aatatacctt attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgttttg      180 gtgtgcgccg gtgtacacag gaagtgacaa ttttcgcgcg gttttaggcg gatgttgtag     240
taaatttggg cgtaaccgag taagatttgg ccattttcgc gggaaaactg aataagagga     300
agtgaaatct gaataatttt gtgttactca tagcgcgtaa tatttgtcta gggccgcggg     360
gactttgacc gtttacgtgg agactcgccc aggtgttttt ctcaggtgtt ttccgcgttc     420
cgggtcaaag ttggcgtttt attattatag tcagctgacg tgtagtgtat ttatacccgg     480
tgagttcctc aagaggccac tcttgagtgc cagcgagtag agttttctcc tccgagccgc     540
tccgacaccg ggactgaaaa tgagacatat tatctgccac ggaggtgtta ttaccgaaga     600
aatggccgcc agtcttttgg accagctgat cgaagaggta ctggctgata atcttccacc     660
tcctagccat tttgaaccac ctacccttca cgaactgtat gatttagacg tgacggcccc     720
cgaagatccc aacgaggagg cggtttcgca gattttttcc gactctgtaa tgttggcggt     780
gcaggaaggg attgacttac tcacttttcc gccggcgccc ggttctccgg agccgcctca     840
cctttcccgg cagcccgagc agccggagca gagagccttg ggtccggttt ctatgccaaa     900
ccttgtaccg gaggtgatcg atcttacctg ccacgaggct ggctttccac ccagtgacga     960
cgaggatgaa gagggtgagg agtttgtgtt agattatgtg gagcaccccg ggcacggttg    1020
caggtcttgt cattatcacc ggaggaatac ggggaccca gatattatgt gttcgctttg    1080
ctatatgagg acctgtggca tgtttgtcta cagtaagtga aaattatggg cagtgggtga    1140
tagagtggtg ggtttggtgt ggtaattttt tttttaattt ttacagtttt gtggtttaaa    1200
gaattttgta ttgtgatttt tttaaaaggt cctgtgtctg aacctgagcc tgagcccgag    1260
ccagaaccgg agcctgcaag acctacccgc cgtcctaaaa tggcgcctgc tatcctgaga    1320
cgcccgacat cacctgtgtc tagagaatgc aatagtagta cggatagctg tgactccggt    1380
ccttctaaca cacctcctga gatacacccg gtggtcccgc tgtgccccat taaaccagtt    1440
gccgtgagag ttggtgggcg tcgccaggct gtggaatgta tcgaggactt gcttaacgag    1500
cctgggcaac ctttggactt gagctgtaaa cgccccaggc cataaggtgt aaacctgtga    1560 ttcgtgtgt ggttaacgcc tttgtttgct gaatgagttg atgtaagttt aataaagggt     1620
gagataatgt ttaacttgca tggcgtgtta aatgggcgg ggcttaaagg gtatataatg     1680
cgccgtgggc taatcttggt tacatctgac ctcatggagg cttgggagtg tttggaagat    1740
```

```
ttttctgctg tgcgtaactt gctggaacag agctctaaca gtacctcttg gttttggagg      1800
tttctgtggg gctcatccca ggcaaagtta gtctgcagaa ttaaggagga ttacaagtgg      1860
gaatttgaag agcttttgaa atcctgtggt gagctgtttg attctttgaa tctgggtcac      1920
caggcgcttt tccaagagaa ggtcatcaag actttggatt tttccacacc ggggcgcgct      1980
gcggctgctg ttgcttttttt gagttttata aaggataaat ggagcgaaga aacccatctg     2040 agcgggggt acctgctgga ttttctggcc atgcatctgt ggagagcggt tgtgagacac       2100
aagaatcgcc tgctactgtt gtcttccgtc cgcccggcga taataccgac ggaggagcag      2160
cagcagcagc aggaggaagc caggcggcgg cggcaggagc agagcccatg gaacccgaga      2220
gccggcctgg accctcggga atgaatgttg tacaggtggc tgaactgtat ccagaactga      2280
gacgcatttt gacaattaca gaggatgggc aggggctaaa gggggtaaag agggagcggg      2340
gggcttgtga ggctacagag gaggctagga atctagcttt tagcttaatg accagacacc      2400
gtcctgagtg tattactttt caacagatca aggataattg cgctaatgag cttgatctgc      2460
tggcgcagaa gtattccata gagcagctga ccacttactg gctgcagcca ggggatgatt      2520
ttgaggaggc tattagggta tatgcaaagg tggcacttag gccagattgc aagtacaaga      2580
tcagcaaact tgtaaatatc aggaattgtt gctacatttc tgggaacggg gccgaggtgg      2640
agatagatac ggaggatagg gtggccttta gatgtagcat gataaatatg tggccggggg      2700
tgcttggcat ggacggggtg gttattatga atgtaaggtt tactggcccc aattttagcg      2760
gtacggtttt cctggccaat accaaccttta tcctacacgg tgtaagcttc tatgggttta     2820
acaatacctg tgtggaagcc tggaccgatg taagggttcg gggctgtgcc ttttactgct      2880
gctggaaggg ggtggtgtgt cgccccaaaa gcagggcttc aattaagaaa tgcctctttg      2940
aaaggtgtac cttgggtatc ctgtctgagg gtaactccag ggtgcgccac aatgtggcct      3000
ccgactgtgg ttgcttcatg ctagtgaaaa gcgtggctgt gattaagcat aacatggtat      3060
gtggcaactg cgaggacagg gcctctcaga tgctgacctg ctcggacggc aactgtcacc      3120
tgctgaagac cattcacgta gccagccact ctcgcaaggc ctggccagtg tttgagcata      3180
acatactgac ccgctgttcc ttgcatttgg gtaacaggag gggggtgttc ctaccttacc      3240
aatgcaattt gagtcacact aagatattgc ttgagcccga gagcatgtcc aaggtgaacc      3300
tgaacggggt gtttgacatg accatgaaga tctggaaggt gctgaggtac gatgagaccc      3360
gcaccaggtg cagaccctgc gagtgtggcg gtaaacatat taggaaccag cctgtgatgc      3420
tggatgtgac cgaggagctg aggcccgatc acttggtgct ggcctgcacc cgcgctgagt      3480
ttggctctag cgatgaagat acagattgag gtactgaaat gtgtgggcgt ggcttaaggg      3540
tgggaaagaa tatataaggt gggggtctta tgtagttttg tatctgtttt gcagcagccg      3600
ccgccgccat gagcaccaac tcgtttgatg gaagcattgt gagctcatat ttgacaacgc      3660
gcatgccccc atgggccggg gtgcgtcaga atgtgatggg ctccagcatt gatggtcgcc      3720
ccgtcctgcc cgcaaactct actaccttga cctacgagac cgtgtctgga acgccgttgg      3780
agactgcagc ctccgccgcc gcttcagccg ctgcagccac cgcccgcggg attgtgactg      3840
actttgcttt cctgagcccg cttgcaagca gtgcagcttc ccgttcatcc gcccgcgatg      3900
acaagttgac ggctcttttg gcacaattgg attctttgac ccgggaactt aatgtcgttt      3960
ctcagcagct gttggatctg cgccagcagg tttctgccct gaaggcttcc tcccctccca      4020
atgcggttta aacataaat aaaaaaccag actctgtttg gatttggatc aagcaagtgt      4080
```

```
cttgctgtct ttatttaggg gttttgcgcg cgcggtaggc ccgggaccag cggtctcggt    4140
cgttgagggt cctgtgtatt ttttccagga cgtggtaaag gtgactctgg atgttcagat    4200
acatgggcat aagcccgtct ctggggtgga ggtagcacca ctgcagagct tcatgctgcg    4260
gggtggtgtt gtagatgatc cagtcgtagc aggagcgctg ggcgtggtgc ctaaaaatgt    4320
ctttcagtag caagctgatt gcca                                           4344

<210> SEQ ID NO 2
<211> LENGTH: 4273
<212> TYPE: DNA
<213> ORGANISM: Homo sapiens

<400> SEQUENCE: 2
catcatcaat aatataccgtt attttggatt gaggccaata tgataatgag gtgggcgggg      60
cgaggcgggg cggtgacgt aggacgcgcg agtagggttg ggaggtgtgg cggaagtgtg     120
gcatttgcaa gtgggaggag ctgacatgca atcttccgtc gcggaaaatg tgacgttttt     180
gatgagcgcc gcctacctcc ggaagtgcca atttcgcgc gcttttcacc ggatatcgta     240
gtaattttgg gcgggaccat gtaagatttg gccattttcg cgcgaaaagt gaaacgggga     300
agtgaaaact gaataatagg gcgttagtca tagcgcgtaa tatttaccga gggccgaggg     360
actttgaccg attacgtgga ggactcgccc aggtgttttt tacgtgaatt ccgcgttcc     420 gggtcaaagt ctccgttttt attgtcgccg tcatctgacg cggagggtat ttaaacccgc     480
tgcgctccta aagaggccac tcttgagtgc cagcgagaag agttttctcc tccgctccgt     540
ttcggcgatc gaaaaatgag acatttagcc tgcactccgg gtcttttgtc cggccgggcg     600
gcgtccgagc ttttggacgc tttgctcaat gaggttctga gcgatgattt tccgtctact     660
acccacttta gcccacctac tcttcacgaa ctgtacgatc tggatgtact ggtggatgtg     720
aacgatccca acgaggaggc ggtttctacg tttttttccg agtctgcgct tttggctgcc     780
caggagggat ttgacctaca cactccgccg ctgcctattt tagagtctcc gctgccggag     840
cccagtggta taccttatat gcctgaactg cttcccgaag tggtagacct gacctgccac     900
gagccgggct ttccgcccag cgacgatgag ggtgagcctt tgcctttaga ctatgctgag     960
atacctgggc tcggttgcag gtcttgtgca tatcatcaga gggttaccgg agaccccgag    1020
gttaagtgtt cgctgtgcta tatgaggctg acctcttcct ttatctacag taagttttt     1080 tgtgtaggtg ggcttttgg gtaggtgggt tttgtggcag gacaggtgta aatgttgctt    1140 gtgtttttg tacctgcagg tccggtgtcc gagccagacc cggagcccga ccgcgatccc    1200
gagccggatc ccgagcctcc tcgcaggcca aggaaattac cttccatttt gtgcaagcct    1260
aagacacctg tgaggaccag cgaggcggac agcactgact ctggcacttc tacctctcct    1320
cctgaaattc acccagtggt tcctctgggt atacatagac ctgttgctgt tagagtttgc    1380
gggcgacgcc ctgcagtaga gtgcattgag gacttgctta acgatcccga gggacctttg    1440
gacttgagca ttaaacgccc taggcaataa acccccaccta agtaataaac cccacctaag    1500
taataaactt taccgcccct ggttattgag atgacgccca atgtttgctt ttgaatgact    1560
tcatgtgtat aataaaagtg agtgtggtca taggtctctt gtttgtctgg gcgggggttta    1620 agggtatata agtttctcgg ggctaaactt ggttacactt gaccccaatg gaggcgtggg    1680
ggtgcttgga ggagttttgcg gacgtgcgcc gtttgctgga cgagagctct agcaatacct    1740
atagtatttg gaggtatctg tggggctcta ctcaggccaa gttggtcttc agaattaagc    1800
aggattacaa gtgcgatttt gaagagcttt ttagttcctg tggtgagctt ttgcaatcct    1860
```

```
tgaatctggg ccaccaggct atcttccagg aaaaggttct ctcgactttg gattttccca      1920
ctcccgggcg caccgccgct tgtgtggctt ttgtgtcttt tgtgcaagat aaatggagcg      1980
gggagaccca cctgagtcac ggctacgtgc tggatttcat ggcgatggct ctttggaggg      2040
cttacaacaa atggaagatt cagaaggaac tgtacggttc cgccctacgt cgtccacttc      2100
tgcagcggca ggggctgatg tttcccgacc atcgccagca tcagaatctg gaagacgagc      2160
gagcggagaa gatcagcttg agagccggcc tggaccctcc tcaggaggaa tgaatctccc      2220
gcaggtggtt gagctgtttc ccgaactgag acgggtcctg actatcaggg aggatggtca      2280
gtttgtgaag aagctgaaga gggatcgggg tgagggagat gatgaggcgg ctagcaattt      2340
agcttttagt ctgataactc gccaccgacc ggaatgtatt acctatcagc agattaagga      2400
gagttgtgcc aacgagctgg atcttttggg tcagaagtat agcatagaac agcttaccac      2460
ttactggctt cagcccgggg atgattggga agaggcgatt agggtgtatg caaaggtggc      2520
cctgcggccc gattgcaagt ataagattac taagttggtt aatattagaa actgctgcta      2580
tatttctgga acgggggccg aagtggagat agatactgag acagggtgg ctattaggtg      2640 ttgcatgata aacatgtggc ccgggatact ggggatggat ggggtgatat ttatgaatgt      2700
gaggttcacg ggccccaact ttaatggtac ggtgttcatg gcaacacca  acttgctcct      2760 gcatggtgcg agtttctatg ggtttaacaa cacctgtata gaggcctgga ccgatgtaaa      2820
ggttcgaggt tgttcctttt atagctgttg gaaggcggtg gtgtgtcgcc ctaaaagcag      2880
gggttctgtg aagaaatgct tgtttgaaag gtgcaccta  ggtatccttt ctgagggcaa      2940
ctccagggtg cgccataatg tggcttcgaa ctgcggttgc ttcatgcaag tgaaggggt     3000 gagcgttatc aagcataact cggtctgtgg aaactgcgag gatcgcgcct ctcagatgct      3060
gacctgcttt gatggcaact gtcacctgtt gaagaccatt catataagca gtcaccccag      3120
aaaggcctgg cccgtgtttg agcataacat tctgacccgc tgttccttgc atctgggggt      3180 caggagggt  atgttcctgc cttaccagtg taactttagc cacactaaaa tcctgctgga      3240
acccgagtgc atgactaagg tcagcctgaa tggtgtgttt gatgtgagtc tgaagatttg      3300
gaaggtgctg aggtatgatg agaccaggac caggtgccga ccctgcgagt gcggcggcaa      3360
gcacatgaga aatcagcctg tgatgttgga tgtgaccgag gagcttaggc ctgaccatct      3420
ggtgctggcc tgcaccaggg ccgagttggg gtctagcgat gaggataccg attgaggtgg      3480
gtaaggtggg cgtggctagc agggtgggcg tgtataaatt gggggtctaa ggggtctctc      3540
tgtttgtctt gcaacagccg ccgccatgag cgacaccggc aacagctttg atggaagcat      3600
ctttagtccc tatctgacag tgcgcatgcc tcactgggcc ggagtgcgtc agaatgtgat      3660
gggttccaac gtgatggac  gtcccgttct gccttcaaat tcgtctacta tggcctacgc      3720
gaccgtggga ggaactccgc tggacgccgc gacctccgcc gccgcctccg ccgccgccgc      3780
gaccgcgcgc agcatggcta cggacctttta cagctctttg gtggcgagca gcgcggcctc      3840
tcgcgcgtct gctcgggatg agaaactgac tgctctgctg cttaaactgg aagacttgac      3900 ccggagctg  ggtcaactga cccagcaggt ttccagcttg cgtgagagca gccttgcctc      3960
cccctaatgg cccataatat aaataaaagc cagtctgttt ggattaagca agtgtatgtt      4020
ctttatttaa ctctccgcgc gcggtaagcc cgggaccagc ggtctcggtc gtttagggtg      4080
cggtggattt tttccaacac gtggtacagg tggctctgga tgtttagata catgggcatg      4140
agtccatccc tggggtggag gtagcaccac tgcagagctt cgtgctcggg ggtggtgttg      4200
```

-continued

```
tatatgatcc agtcgtagca ggagcgctgg gcgtggtgct gaaaaatgtc cttaagcaag    4260
aggcttatag cta                                                       4273

<210> SEQ ID NO 3
<211> LENGTH: 19
<212> TYPE: DNA
<213> ORGANISM: Homo sapiens

<400> SEQUENCE: 3
tccctatcag tgatagaga                                                   19
```

EUKARYOTIC CELL LINE

CROSS-REFERENCE TO RELATED APPLICATIONS

This application is a U.S. national phase of International Application No. PCT/EP2018/079341, filed on Oct. 25, 2018, which claims priority to European Patent Application No. 17198339.8, filed Oct. 25, 2017, both of which are incorporated by reference herein in their entirety.

The present invention relates to a cell line, use of the cell line and a method for producing infectious viral particles using said cell line.

BACKGROUND OF THE INVENTION

Novel vaccines are needed for the prevention or treatment of diseases such as HIV, hepatitis C, malaria, tuberculosis, and cancers. Preclinical and clinical evidence supports the role of T cell immunity and, in particular, CD8+ T cells in the clearance of these diseases. One way to induce a CD8+ T cell response against a particular antigen is to express that antigen and suitable pathogen-derived innate activators intracellularly through gene delivery; genetic or gene-based vaccines coopt physiological antigen processing and major histocompatibility complex (MHC) class I presentation to activate a CD8+ T cell response. Replication-defective adenovirus vectors have been extensively used for genetic vaccine by substituting the essential E1 region with the expression cassette for the antigen. Ad vectors are attractive as gene delivery system because they infect both replicating and non-replicating cells, have a broad tissue tropism, propagate very efficiently in the available packaging cell lines, and have a scalable and affordable production process. Indeed, Ad-based vectors elicit more potent antigen-specific CD8+ T cells than other genetic vaccine vectors based on poxviruses, lentiviruses, alphavirus, and naked DNA in animal models and human clinical trials. However, successful development of adenovirus vectors as genetic vaccine carriers will eventually depend not only on their immunological potency but also on the availability of cell substrates for scalable and reproducible production processes. Adenoviral vectors are able to expresses high levels of the antigenic protein they deliver not only in the target tissue in vivo but also during the production process in the complementing cell line. In the current vector system, the transgene expression is driven by the strong human cytomegalovirus immediate/early promoter (HCMV promoter) that allows high level of transgene expression not only in the target tissue but also in the packaging cell line during the vector production process. We have several evidences indicating that the high transgene expression in the packaging cell line can interfere with the adenovirus replication. In our extensive experience with adenoviral vector rescue and propagation, we have observed detrimental effects on virus replication mediated by transgene over-expression ranging from reduced vector yields to complete inhibition of replication. In addition, the interference with the vector replication can lead to the genetic instability of the vector itself with the selection of rearranged vector species The development of a cell line capable to repress the expression of the transgene carried by an adenoviral vector during the production process may prevent the negative effects of the transgene overexpression. Therefore, the system is based on a cell line expressing high levels of TetR and by Ad vectors carrying a transgene under control of human cytomegalovirus promoter or other strong promoters such as CASI promoter, CAG promoter, EF1α promoter with two or more copies of TetR binding sites inserted downstream the promoter TATA box.

SUMMARY OF THE INVENTION

In a first aspect, the present invention provides a cell line, wherein a tetracycline repressor (Tet-R) is expressed under the control of a cellular or partly cellular promoter.

In a second aspect, the invention relates to a use of the cell line according to the first aspect of the invention for producing infectious viral particles.

In a third aspect, the invention relates to a method for producing infectious viral particles comprising the steps of:
(i) growing the cells of the cell line of the first aspect of the invention further comprising a viral genome capable of assembling into an infectious viral particle in vitro in the absence of tetracycline or a tetracycline analog; or
(ii) infecting the cells of the cell line of the first aspect of the invention with a viral vector, preferably an adenoviral vector; and
(iii) recovering the viral particles.

LIST OF FIGURES

In the following, the content of the figures comprised in this specification is described. In this context please also refer to the detailed description of the invention above and/or below.

FIG. 1: Diagram of pneo/CAG-TetR. Pneo/CAG-TetR contains the expression cassette for the Tetracycline repressor and G418-resistance gene.

Figure 2:
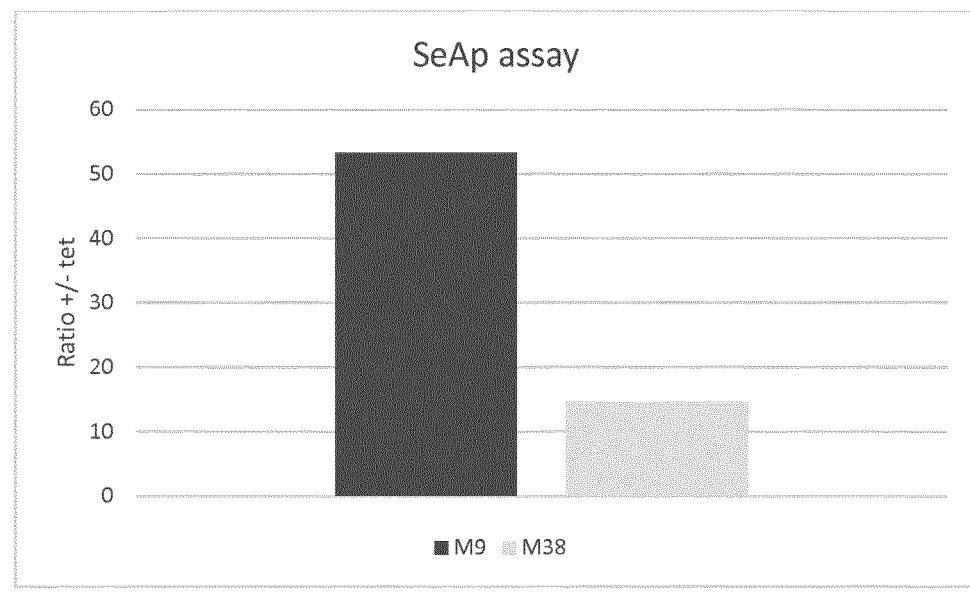

FIG. 2: SeAP expression in clone M9 and M38. Clones were seeded in flasks T25 and infected with ChAdETetO-Seap at moi 30 (multiplicity of infection) in presence or absence of tetracycline. A score for each single clone was then obtained by calculating the ratio with and without tetracycline 48 h post infection. Clone M9 showed the best ratio+/−tet.

Figure 3:
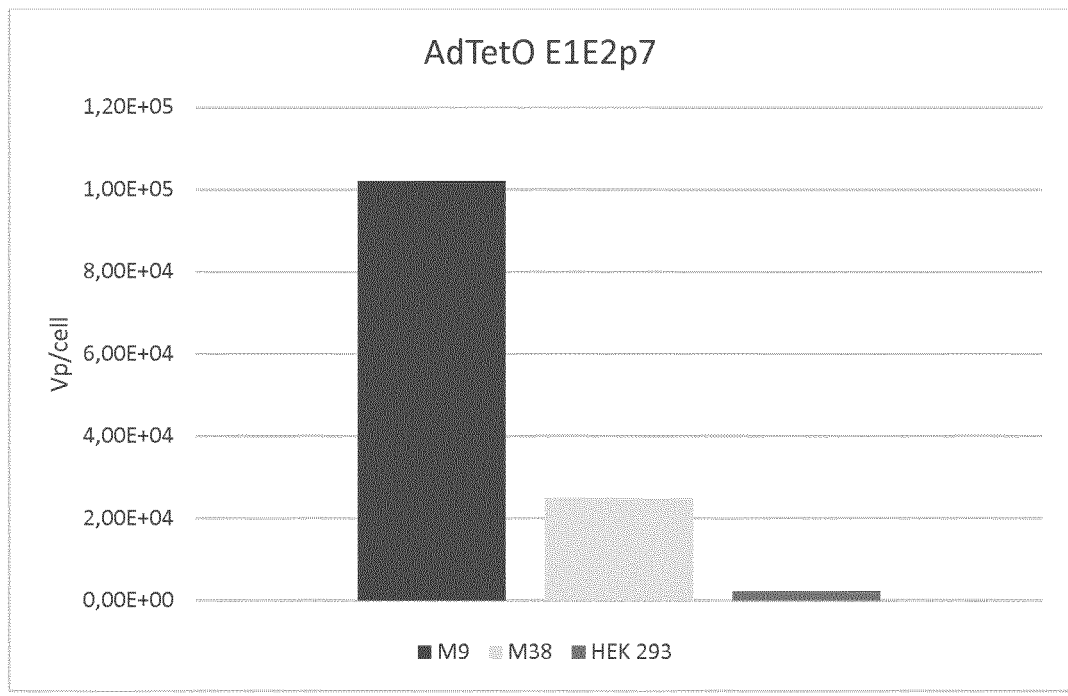

FIG. 3: Production of AdTetO E1E2p7 in M9, M38 and Hek293 cells. M9, M38 and HEK 293 were infected at moi 100 (multiplicity of infection) with AdTetOE1/F78E2p7 (An Adenovector that is not able to grow without TetR mediated control of expression). Clones M9 and M38 show the best productivity values.

Figure 4:
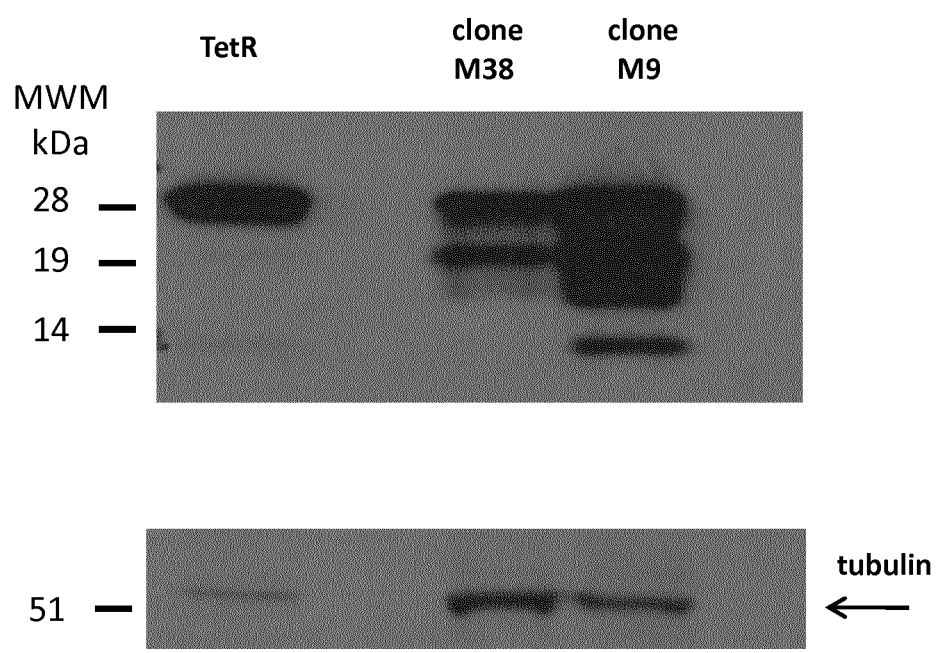

FIG. 4: Expression of TetR protein in M9 and M38 cells. TetR expression was evaluated by Western blot analysis on cell lysate of clone M9 and M38 using TetR antibody. TetR is expressed at high levels in both M9 and M38 cells.

Figure 5:
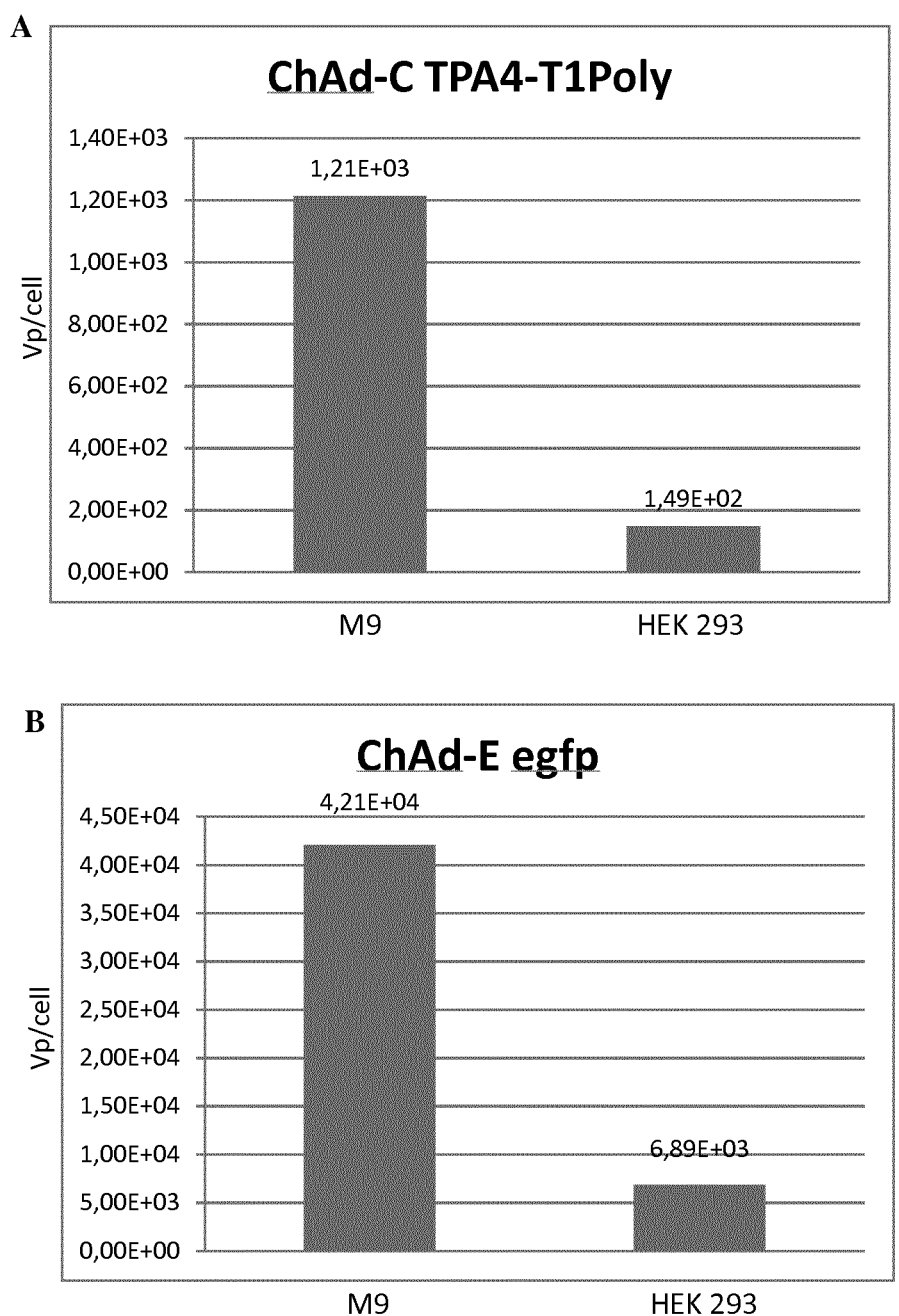

FIG. 5: Efficiency of rescue of ChAd vectors in M9 cells. The efficiency of rescue of Species C and E adenoviral vectors (ChAdN13 TPA4-T1Poly (FIG. 5A) and ChAdE egfp (FIG. 5B)) was evaluated in M9 cells in comparison to HEK-293. Monolayers of M9 and HEK293 cells were transfected in parallel with preAd plasmid DNA. The virus production was evaluated by QPCR 12 days post-transfection on cell lysates. The results demonstrate a higher efficiency of adenoviral vector production in M9 cells upon transfection.

Figure 6:
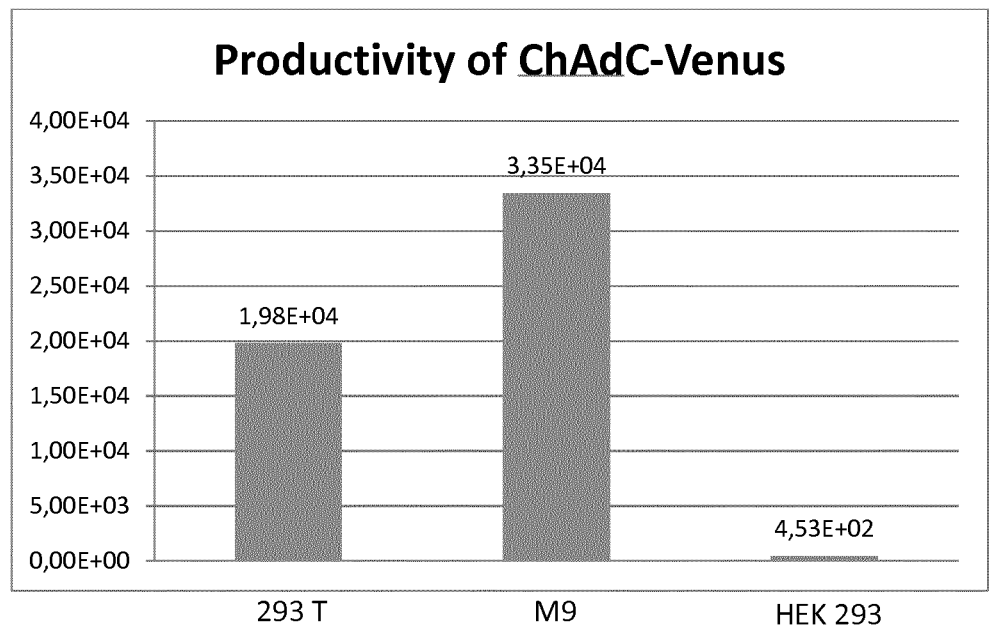
Figure 6:
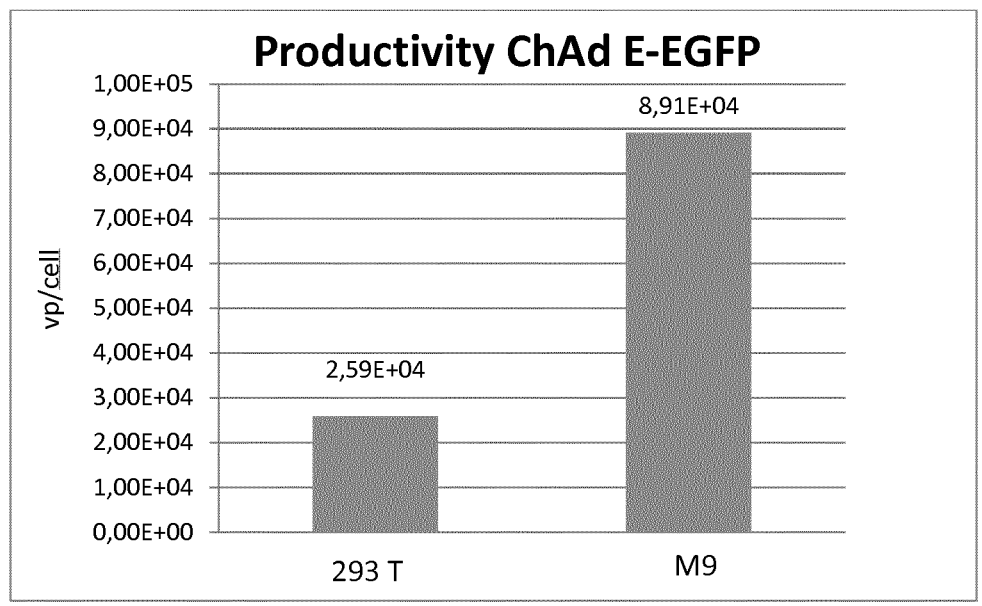

FIG. 6: Productivity of ChAd C-Venus and ChAd E-EGFP vectors. The productivity of chimpanzee Ad vectors ChAd C-Venus (FIG. 6A) and ChAd E-EGFP (FIG. 6B) was evaluated in M9 cells in comparison to HEK 293 and 293T cells. Monolayers of cells were infected using the same multiplicity of infection of ChAds. The cells were harvested 72 hours post-infection and the vector titer was evaluated by QPCR in the crude lysate. The results are expressed as cell-specific productivity.

Figure 7:
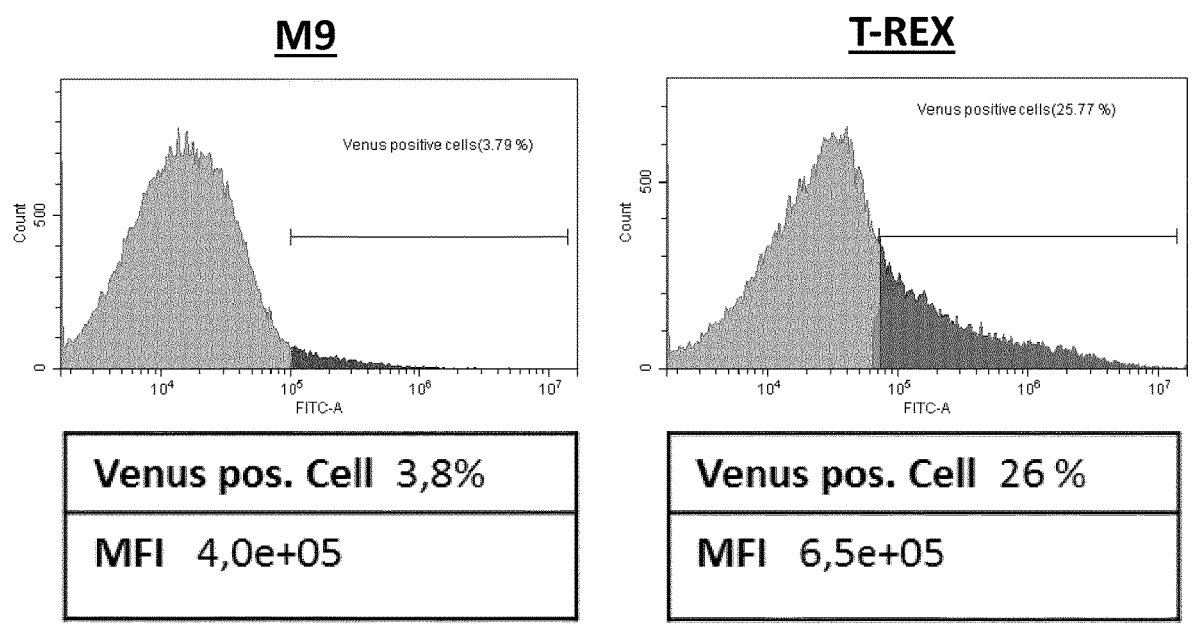

FIG. 7: Evaluation of transcriptional control in M9 and T-Rex cells by FACS analysis. Cell lines were seeded in T25 flasks and infected with ChAd C TetO-VENUS using a moi=100 vp/cell (multiplicity of infection). The expression of sufficient amount of TetR at single cell level should shut-off venus reporter gene expression. 3.8% of M9 cells showed a detectable fluorescent signal versus 26% of T-Rex cells. M9 cell line was demonstrated to be able to control gene expression in 96.2% of the cells while 74% of T-Rex cells efficiently control expression.

Figure 8:
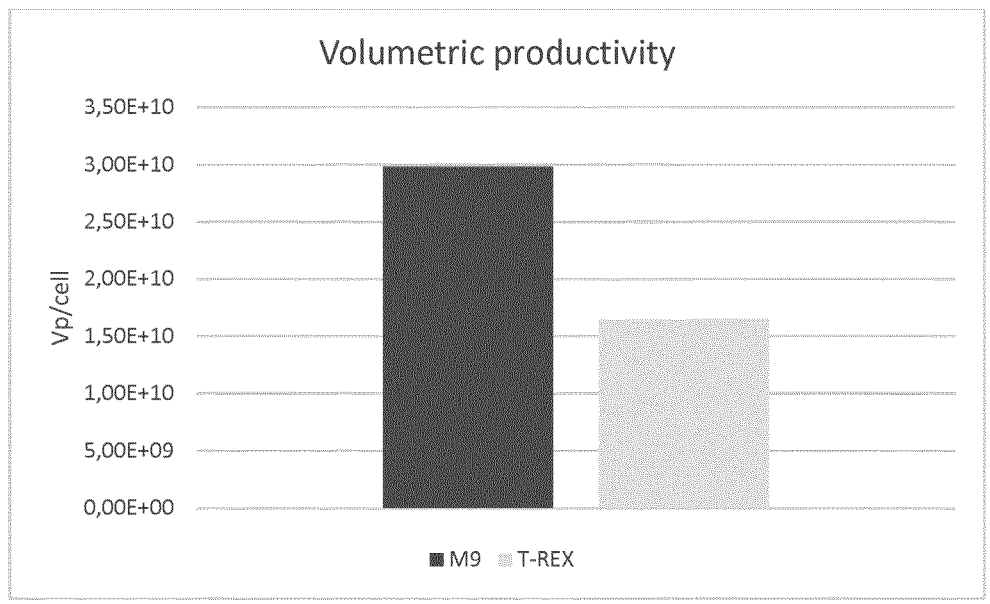
Figure 8:
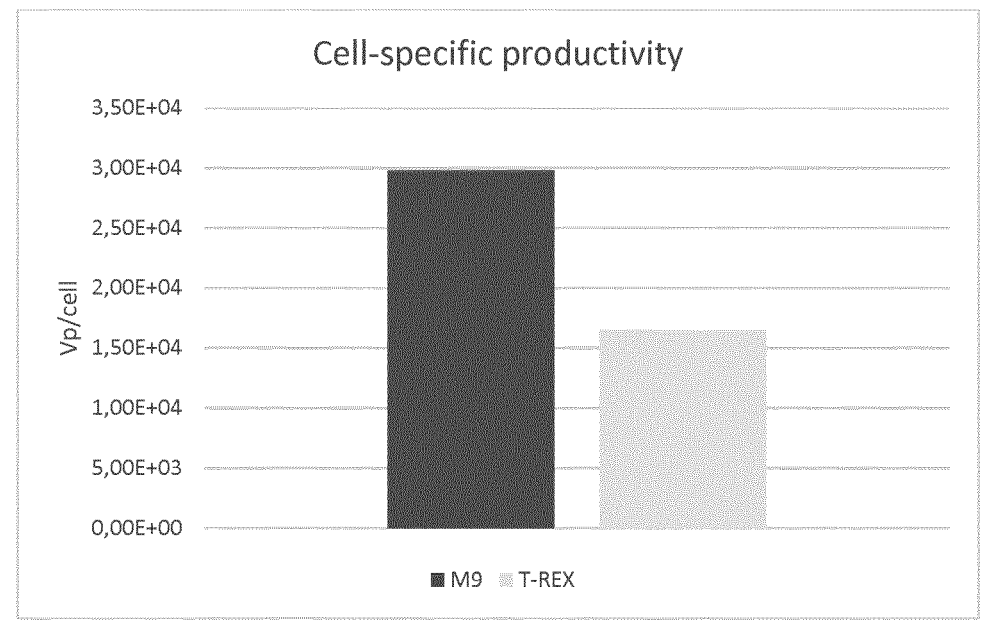

FIG. 8: ChAd vector productivity in M9 (FIG. 8A) and T-Rex (FIG. 8B) cell lines. The analysis was performed in cell seeded in T-flasks (T25 flasks seeded with 5e6 cells in 10 ml of medium). Cell monolayers were infected with ChAd-C TetO-VENUS using a multiplicity of infection of 100 vp/cell. Cells were harvested when full CPE was observed by microscopy (7 days post-infection). The vector productivity was determined by QPCR method with primers and probe designed of HCMV promoter DNA sequence.

Figure 9:
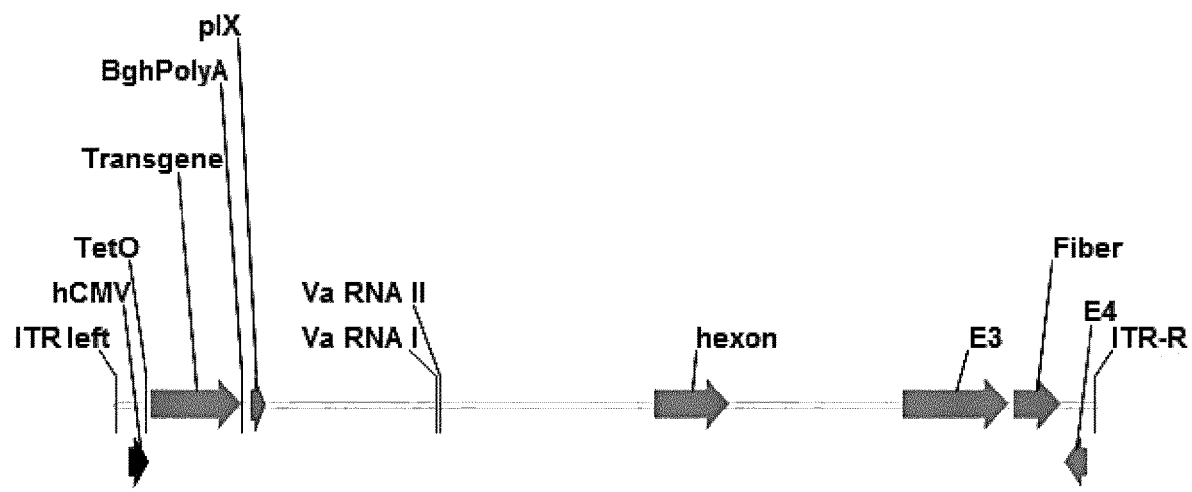
Figure 9:
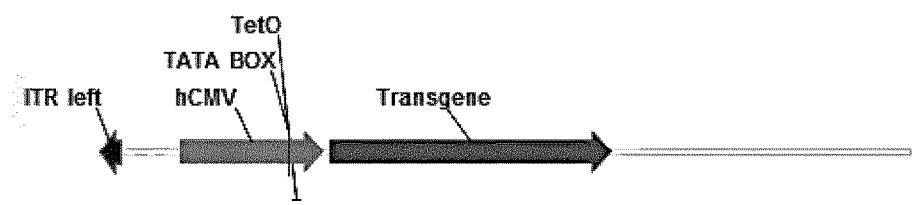

FIG. 9: Diagram of an adenoviral vector and of the expression cassette. The adenoviral vector is carrying a HCMV promoter with TetO and the expression cassette includes TetO sequences.

Figure 10:

FIG. 10: TetR expression driven by CAG promoter in comparison to HCMV-driven expression. HCMV-TetR 293 cells were first developed by transfecting HCMV-TetR expression vector in HEK 293 cells. A clone expressing TetR was isolated by G418 selection and expanded. TetR expression was tested by western blot at passage 40 and at passage 60 and compared to TetR expression in M9 cells at passage 60. Total cell proteins were extracted from 3E+06 cells, separated on SDS-PAGE, transferred to the membrane and probed with anti-TetR antibody (antibody dilution:1:1000, incubation for 12 hours at 4° C.). The results demonstrated that TetR expression driven by HCMV promoter is progressively lost over cell culture passaging while the TetR expression driven by CAG promoter is maintained over-passaging (p60).

Figure 11:
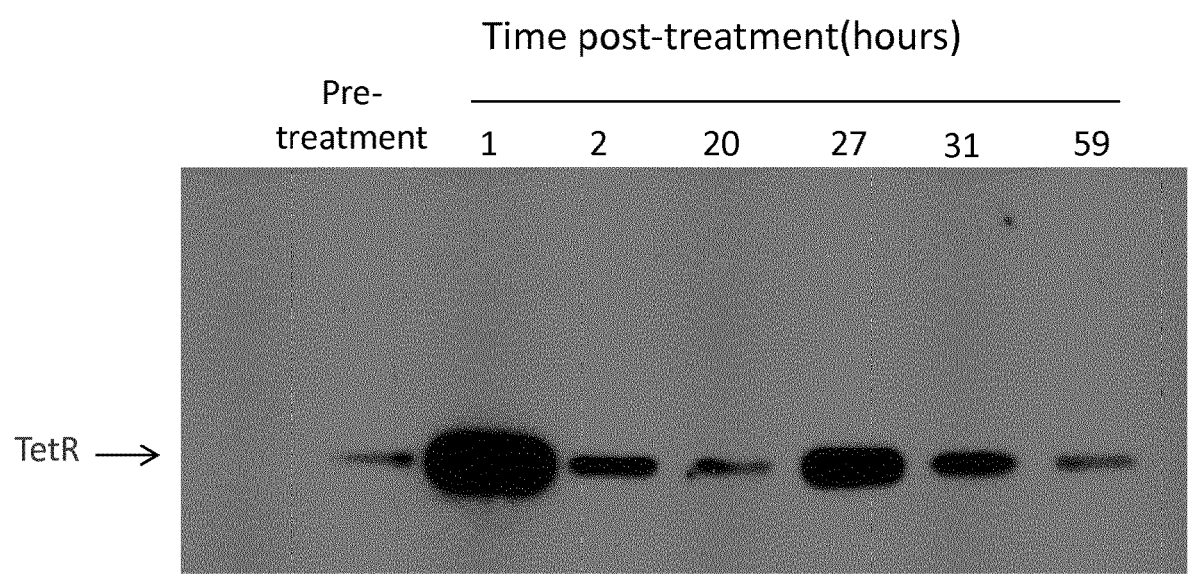

FIG. 11: HCMV promoter silencing by epigenetic mechanisms. The gradual loss of TetR expression observed in HCMV-TetR cell line can be reverted by exposing the cells to HDAC inhibitors (Belinostat). The HCMV TetR cells were cultivated in presence of 200 nM of Belinostat (PXD101—HDAC inhibitor), then the TetR expression was evaluated by western blot by harvesting the cells. However the re-activation of the human CMV promoter is transient and the expression of TetR is lost again in absence of Belinostat.

DETAILED DESCRIPTIONS OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IU-PAC Recommendations)", Leuenberger, H. G. W, Nagel, B. and Klbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. In the following passages, different aspects of the invention are defined in more detail. Each aspect so defined may be combined with any other aspect or aspects unless clearly indicated to the contrary. In particular, any feature indicated as being optional, preferred or advantageous may be combined with any other feature or features indicated as being optional, preferred or advantageous.

Several documents are cited throughout the text of this specification. Each of the documents cited herein (including all patents, patent applications, scientific publications, manufacturer's specifications, instructions etc.), whether supra or infra, is hereby incorporated by reference in its entirety. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

In the following, the elements of the present invention will be described. These elements are listed with specific embodiments; however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Definitions

In the following, some definitions of terms frequently used in this specification are provided. These terms will, in each instance of its use, in the remainder of the specification have the respectively defined meaning and preferred meanings.

As used in this specification and the appended claims, the singular forms "a", "an", and "the" include plural referents, unless the content clearly dictates otherwise.

The term "expresses a gene" or "expresses a protein" is used in the context of the present invention to refer to the process of mRNA transcription followed by translation of the mRNA into the encoded protein. The expression level can be measured at the level of the mRNA and/or protein. If measured at the level of mRNA the amount of mRNA will provide at least a qualitative indication of the amount of the protein present in the cell. In the majority of cases all mRNA will be translated into protein and, thus the measurement of the amount of mRNA allows quantitating the amount of newly produced protein. The amount of protein can be determined by a number of art known methods including labelling with antibodies specifically binding to the protein. The skilled person knows several ways of qualitatively and/or quantitatively detecting expression of a gene on single cell basis. These methods include FISH, intracellular staining (ICS) and single cell RNA sequencing.

The term "mutation" as used in the context of the present invention refers to the exchange of a nucleotide or amino acid with another nucleotide in a nucleic acid sequence and with amino acid in an amino acid sequence, respectively. The term "deletion" as used in the context of the present invention refers to the removal of a nucleotide from a nucleic acid sequence and of an amino acid in an amino acid sequence, respectively. The term "insertion" as used in the context of the present invention refers to the addition of a nucleotide to a nucleic acid sequence and of an amino acid to an amino acid sequence. A substitution can also be viewed as a consecutive process of insertion and deletion or vice versa. In the context of the present invention the term substitution is used to an alteration of a nucleic acid sequence or amino acid sequence which does not change the number of nucleotides of the nucleic acid sequence or the number of amino acids in the amino acid sequence.

The term "immortal" or "immortalized" as used in the context of the invention refers to the property of a cell to divide indefinitely. An immortalized cell will grow into a population of cells also referred to a "cell line". Preferably, such a cell line comprises or consists of isolated cells. Preferably, such a cell line will not become senescent. Preferably, it will also not enter apoptosis under cell culture conditions. While a cell line is typically of clonal origin, i.e. all cells are descendants of one transformed cell, it is common that there is heterogeneity within a cell line. This is due to chromosomal re-arrangements, chromosome duplications, or improper chromosomal separation that may occur during mitosis. Such events are more common in transformed cells. The term "transformed" refers to an additional property of a cell line, i.e. in addition to infinite growth. These properties are one or more that are associated with tumor cells, including anchorage independent growth, loss of contact-inhibition, invasiveness, and polyploidy. Preferably, the transformed cell line is transformed by an adenovirus or an adenoviral particle.

The term "cell line" refers to a cell line that exhibits heterogeneity regarding one or more properties. Typically, the heterogeneity does not change significantly or at all during subsequent mitotic cycles of the cells of the cell line A particular property regarding which the cell line may be heterogeneous is the expression of a given transgene, preferably the Tet-R and/or the ploidy.

The term "Tet-R" is used in the context of the invention to refer to the Tetracycline repressor.

The terms "TRE" and "TetO" are used to designate DNA elements to which the Tet-R specifically binds. Preferably, the TetO sequence is the nucleotide sequence of SEQ ID NO:3 (TCCCTATCAGTGATAGAGA).

If TetO is inserted in multiple copies into or close to the basal promoter of a gene, Tet-R can act as a repressor of transcription from that basal promoter. To maximize the effect of Tet-R binding it is often desirable to include two or more TetOs consecutively into one promoter. Preferably, two, three, four, five, six to at least 7 copies of TetOs are consecutively included into one promoter.

The term "heterologous gene" is used in the context of the present invention to refer to a gene that is either non-naturally occurring or taken out of its natural context and inserted into either a different position within the genome where it naturally occurs or into another organism or genome. For example, a human gene encoding a tumor antigen that is inserted into an adenoviral genome is heterologous to the adenoviral genome.

The term "toxic" is used in the context of the present invention to refer to the activity of a compound to inhibit proliferation of a cell line. Depending on the compound and concentration that inhibition can be complete, i.e. the individual cells stops growing, or they go into apoptosis.

The term "viral particles" is used in the context of the present invention to refer to a virus, preferably a recombinant virus or a virion that comprises a nucleic acid sequence. This nucleic acid sequence may be a full or partial viral genome. In the latter case the viral genome preferably comprises a heterologous gene. For some viral particles only very short sequences of the viral genome are required to allow assembly of a virus or virion. For example, for adeno-associated virus a short (about 200 bp long) repeat sequence placed at the 5' and 3' of a heterologous nucleic acid of a given length (typically between 4.5. to 5.3 kB for an adeno-associated virus) will allow assembly of infectious adeno-associated virus. A viral particle is "infectious" in the meaning of the invention, if it can transfer the nucleic acid contained therein into a cell, if contacted with the cell.

A preferred cell line of the invention is the HEK293 derived cell line referred to as M9. This cell line was deposited on Aug. 9, 2017 with the European Collection of Authenticated Cell Cultures (ECACC) at Public Health England, Culture Collections, Porton Down, Salisbury SP4 0JG, United Kingdom under the accession number 17080901. The deposit was made on behalf of Nouscom AG, Baumleingasse 18, Basel, CH-4051, Switzerland. The cell line is derived from an early passage human embryonal kidney cell line (*Homo Sapiens*).

EMBODIMENTS

In the following different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

In the work leading to the present invention, it was surprisingly shown that good adenoviral vector productivity can be achieved by the cell line according to the present invention.

In a first aspect, the present invention provides a cell line, wherein a tetracycline repressor (TetR) is expressed under the control of a cellular or partly cellular promoter. It also provides a cell line, wherein a tetracycline repressor (TetR) is expressed in at least 70% of the cells of the cell line. Preferably, at least 75%, more preferably at least 80%, and more preferably at least 85%, more preferably at least 90% and most preferably at least 95% of the cells within the cell line(s) express Tet-R. The percentage of cells within the cell line(s) of that express Tet-R can be measured by art known methods including fluorescent staining of proteins or mRNA and FACS analysis.

The level of gene expression per cell can be measured by quantitative polymerase chain reaction (QPCR), preferably single cell QPCR. The quantitative polymerase chain reaction is a known method for one skilled in the art. For reference, it is referred to Applied Biosystems QuantStudio™ 12K Flex Real-Time PCR System—Publication Part Number 4470050 Rev. A Revision Date March 2012.

In a preferred embodiment of the first aspect of the present invention, the Tet-R is expressed in those cells of the cell line expressing Tet-R protein at a level of at least $10^3$ protein molecules/cell, preferably at least $10^4$ protein molecules/cell, preferably at least $10^5$ protein molecules/cell, preferably at least $10^6$ protein molecules/cell, more preferably at least $10^7$ protein molecules/cell, such as from $10^3$ to $10^6$, $10^4$ to $10^5$ protein molecules/cell. Correspondingly, it is preferred that the cell line expressing Tet-R protein comprises between $10^3$ to $10^6$, more preferably $10^4$ to $10^5$ mRNA copies per cell.

In a preferred embodiment of the first aspect of the present invention, the cell line comprises stably integrated into its genome a gene encoding tetracycline repressor (Tet-R). Preferably, the gene encoding Tet-R is only stably integrated into the cells that express Tet-R. Preferably, the gene encoding Tet-R is stably integrated in at least 70%, preferably 75%, 80% or 85% of the cells of the cell line. More preferably, at least 90%, even more preferably at least 95%, and most preferably at least 97% of the cells within the cell line comprise stably integrated into its genome a gene encoding Tet-R.

In a preferred embodiment of the first aspect of the present invention, the expression of Tet-R is stable over time. "Time" in context of the present invention can be defined as the number of cell passages of the cell line. Therein, 10 passages correspond to about 30 to 70 days, preferably to 40-60 days and more preferably to about 50 days. Within this time frame of 10 days, 5 passages can, but do not necessarily correspond to 15-35 days, preferably 20-30 days and more preferably 25 days. Within the time frame of 10 days, 1 passage can, but does not necessarily correspond to 3-7 days, preferably 4-6 days and more preferably 5 days. Preferably, stable over time means stable for at least 40 (or more than 40) passages, for at least 45 (or more than 45) passages, for at least 50 (or more than 50) passages, for at least 60 (or more than 60) passages or for at least 75 (or more than 75) passages. For all these embodiments, the expression is preferably stable for up to and including 100 passages. The number of corresponding days can be calculated for these and any other number of passages using the definition given for 10, 5 and/or 1 days above. For example, 40 passages correspond to 120-280 days, preferably 160-240 days and more preferably 200 days; 45 passages correspond to 135-315 days, preferably 180-270 days and more preferably 225 days; 50 passages correspond to 150-350 days, preferably 200-300 days and more preferably 250 days; 60 passages correspond to 180-420 days, preferably 240-360 days and more preferably 300 days; 75 passages correspond to 225-525 days, preferably 300-450 days and more preferably 375 days; 100 passages correspond to 300-700 days, preferably 400-600 days and more preferably 500 days. The upper limits embodiments are combined with the lower limits according to their ranking of preference. "Time" also be defined independent of passages by the number of days only. In this case, the ranges above given with respect to the number of passages apply as embodiments (for example, "120-280 days" refers to an embodiment of "at least 120-280 days", which is not limited by any number of passages, i.e. it could be less or more than 40 passages; the preferred ranges then represent preferred embodiments). "Stable" herein means an increase of decrease of not more than 50%, preferably not more than 25%, and more preferably of not more than 10% of the average expression level during passages 10-20. In a preferred embodiment of the first aspect of the present invention, the Tet-R represses transcription of genes comprising in their promoters one or more Tetracycline Operators (TetOs) in the presence or absence of tetracycline or a tetracycline analog. For example, the promotor comprises 1, 2, 3, 4, 5, 6, 7 or more TetOs.

In a preferred embodiment of the first aspect of the present invention, the Tet-R gene is under the control of a constitutive promoter. In a further preferred embodiment, the constitutive promoter is selected from the group consisting of EF1 alpha promoter, PGK-1 promoter, Ubiquitin B promoter, β-Actin promoter, EGR1 promoter, HCMV promotor, SV40 promoter, RSV promoter, mouse CMV promoter, CASI promoter and CAG promoter. More preferably, the Tet-R gene is under the control of the CAG promoter. The promotor is preferably a cellular or a partly cellular promoter. A cellular promoter is preferably a promoter of a eukaryotic cell. Preferably, the promoter is a cellular promoter or a partly cellular promoter. Examples of cellular promoters are mouse, rat, rabbit, guinea pig, chicken and in particular human promoters. "Partly cellular promoters" are hybrid promoters comprising part(s) of one or more cellular promoter(s) and part(s) of one or more non-cellular promoter(s). The non-cellular promoter is preferably a viral promoter. The cellular and non-cellular parts are a fusion that has promoter activity (activity that results in the transcription of a coding sequence of interest). Preferred cellular promoters are the EF1 alpha promoter, the PGK-1 promoter, the Ubiquitin B promoter, the β-Actin promoter, and the EGR1 promoter. Preferred partly cellular promoters are the CASI promoter (partly cytomegalovirus and partly chicken) and the CAG promoter. The CAG promoter (the promoter used in the M9 cells of the examples) is most preferred. It comprises (C) the cytomegalovirus early enhancer element, (A) the promoter, the first exon and the first intron of the chicken beta-actin gene, and (G) the splice acceptor of the rabbit beta-globin gene.

The promoters comprising one or more Tetracycline Operators (TetOs), which can be repressed by Tet-R, are not particularly limited, e.g. they can be cellular, partly cellular, viral or partly viral (hybrid promoters comprising a part of a viral promoter and a part of a non-viral promoter) promoters.

In another preferred embodiment, the gene encoding Tet-R is codon optimized for expression in eukaryotic (preferably mammalian) cells. Herein, the term "codon optimized" means that the translational efficiency for expression in eukaryotic (preferably mammalian) cells is increased by replacing codons which have a low frequency in eukaryotic (preferably mammalian) cells by codons that translate into the same amino acid, but which have a high frequency in eukaryotic (preferably mammalian) cells.

In a further preferred embodiment, the cell line further comprises in its genome a mutation, deletion or insertion that reduces or prevents expression of a functional protein selected from the group consisting of stimulator of one or more IFN genes, preferably cGas and STING, one or more JAK/STAT activator of transcription and one or more IFN-stimulated genes (ISGs), preferably PKR, MX1, OAS1, APOBEC3G, TRIM5, ZAP, ISG15, ADAR, IFITM1/2/3, BST2, and/or RSAD2.

In a preferred embodiment of the first embodiment of the present invention, the cell line further comprises a gene encoding a selection marker. Preferably, the resistance gene is in genetic linkage to the gene encoding Tet-R. In a preferred embodiment, the gene encoding a selection marker is selected from the group consisting of a G418, hygromycin B, puromycin, blasticidin, or zeocin resistance gene in genetic linkage to the gene encoding Tet-R. More preferably, the gene encoding a selection marker is a G418 resistance gene in genetic linkage to the gene encoding Tet-R.

In a further preferred embodiment, the cell line expresses at least one viral gene that is required for the formation of infectious virus particles. More preferably if the cell line is used for production of recombinant adenoviruses, the at least one viral gene is E1-A and/or E1-B as encoded in the E1 region. For example, the E1 regions can be derived from human adenoviruses or great apes adenoviruses, such as Chimpanzee Ad, Bonobo Ad, or Gorilla Ad. More preferably, the cell line comprises in its genome a nucleotide sequence selected from the group consisting of SEQ ID NO: 1 or 2, or a variant thereof encoding the same E1-A and/or E1-B protein.

In a preferred embodiment, the cells of the cell line are transformed cells.

In a further preferred embodiment, the cells of the cell line are human cells. More preferably, the cells of the cell line are human embryonal kidney cells.

In a preferred embodiment, the cells of the cell line are selected from the group consisting of HEK293 cells, A549 cells, HeLa cells, MRC5 cells, VERO cells, DF-1 cells or SK-OV-3 cell.

In another preferred embodiment, the cell line is the cell line deposited under accession number 1708091 with the ECACC.

In a further preferred embodiment, the cell line further comprises a viral genome capable of assembling into an infectious viral particle and comprising at least one heterologous gene under the control of a promoter comprising one or more Tetracycline Operators (TetO).

In another preferred embodiment, the viral genome is selected from the group consisting of a herpes virus genome, a modified vaccinia Ankara genome and an adenoviral genome. More preferably, the viral genome is an adenoviral genome. An example of a herpes virus genome is HSV-1.

In a preferred embodiment, the heterologous gene is toxic to the cell or interferes with the viral replication cycle.

In another preferred embodiment, the heterologous gene is selected from the group consisting of self antigens, viral genes, genes of cellular origin, synthetic strings encoding for combination of tumor-associated neo-antigens and strings encoding for neo-epitopes. Preferably, the self antigen is selected from the group consisting of HER2/neu, CEA, Hepcam, PSA, PSMA, Telomerase, gplOO, Melan-A/MART-1, Muc-1, NY-ES0-1, Survivin, Stromelysin 3, Tyrosinase, MAGE3, CML6S, CML66, OY-TES-1, SSX-2, SART-1, SART-2, SART-3, NYC0-5S, NY-BR-62, hKLP2 and VEGF. Preferably, the viral gene is selected from the group consisting of HCV E1-E2 protein, rabies glycoprotein, and HIV-1 GP 160. Preferably, the gene of cellular origin is selected from the group consisting of Tim-3, Her2 and E2 F-1.

The second aspect of the invention provides use of the cell line according to the first aspect of the invention for producing viral particles.

The third aspect of the invention provides a method for producing infectious viral particles comprising the steps of:
  (i) growing the cells of the cell line of the first aspect of the invention further comprising a viral genome capable of assembling into an infectious viral particle in vitro in the presence or absence of tetracycline or a tetracycline analog; or
  (ii) infecting the cells of the cell line of the first aspect of the invention with a viral vector, preferably an adenoviral vector; and
  (iii) recovering the viral particles.

In a preferred embodiment of the third embodiment of the present invention, the growing step (i) is in the absence of tetracycline or a tetracycline analog.

The invention relates inter alia to the following items:
1. A cell line, wherein a tetracycline repressor (Tet-R) is expressed in at least 70% of the cells of the cell line.
2. The cell line according to item 1, wherein the Tet-R is expressed in those cells of the cell line expressing Tet-R at a level of at least 1000 mRNA copies or Tet-R protein molecules per cell.
3. The cell line according to item 1 or 2, comprising stably integrated into its genome a gene encoding tetracycline repressor (Tet-R).
4. The cell line according to any of items 1 to 3, wherein
  (i) the Tet-R represses transcription of genes comprising in its promoters one or more Tetracycline Operators (TetOs) in the presence or absence of tetracycline or a tetracycline analog, and/or
  (ii) the Tet-R gene is under the control of a constitutive promoter, preferably the constitutive promotor is selected from the group consisting of EF1 alpha promoter, PGK-1 promoter, Ubiquitin B promoter, β-Actin promoter, EGR1 promoter, HCMV promotor, SV40 promoter, RSV promoter, mouse CMV promoter, CASI promoter and CAG promoter, more preferably the constitutive promotor is the CAG promoter.
5. The cell line according to any of items 1 to 4, wherein the gene encoding Tet-R is codon optimized for expression in mammalian cells.
6. The cell line according to any of items 1 to 5, further comprising in its genome a mutation, deletion or insertion that reduces or prevents expression of a functional protein selected from the group consisting of one or more stimulator of an IFN gene, preferably cGas and STING, one or more JAK/STAT activator of transcription and one or more IFN-stimulated gene (ISG), preferably PKR, MX1, OAS1, APOBEC3G, TRIM5, ZAP, ISG15, ADAR, IFITM1/2/3, BST2, and/or RSAD2.
7. The cell line according to any of items 1 to 6, further comprising a gene encoding a selection marker, preferably a G418, hygromycin B, puromycin, blasticidin, or zeocin resistance gene in genetic linkage to the gene encoding Tet-R.
8. The cell line according to any of items 1 to 7, wherein the cells of the cell line express at least one viral gene that is required for the formation of infectious virus particles, preferably wherein the at least one viral gene is selected from the group consisting of E1, preferably comprising a gene with the nucleotide sequence of SEQ ID NO: 1.
9. The cell line according to any of items 1 to 8, wherein the cells of the cell line are human cells, preferably human embryonal kidney cells.
10. The cell line according to item 8 or 9, wherein the cells of the cell line are HEK293 cells, A549 cells, HeLa cells, MRC5 cells, VERO cells, DF-1 cells or SK-OV-3 cells.
11. The cell line according to any of items 1 to 10, wherein said cell line is deposited under accession number 17080901 with the ECACC.
12. The cell line according to any of items 1 to 11, further comprising a viral genome capable of assembling into an infectious viral particle and comprising at least one heterologous gene under the control of a promoter comprising one or more Tetracycline Operators (TetO), preferably wherein
  (i) the viral genome is selected from the group consisting of a herpes virus genome, a modified vaccinia Ankara genome and an adenoviral genome, preferably, the viral genome is an adenoviral genome and/or (ii) the heterologous gene is toxic to the cell.

13. The cell line according to item 12, wherein the heterologous gene is selected from the group consisting of self antigens, viral genes, genes of cellular origin, synthetic strings encoding for combination of tumor-associated neo-antigens and strings encoding for neo-epitopes, preferably wherein (i) the self antigen is selected from the group consisting of HER2/neu, CEA, Hepcam, PSA, PSMA, Telomerase, gplOO, Melan-A/MART-1, Muc-1, NY-ES0-1, Survivin, Stromelysin 3, Tyrosinase, MAGE3, CML6S, CML66, OY-TES-1, SSX-2, SART-1, SART-2, SART-3, NYC0-5S, NY-BR-62, hKLP2 and VEGF, (ii) the viral gene is selected from the group consisting of HCV E1-E2 protein, rabies glycoprotein, and HIV-1 GP 160, and/or (iii) the gene of cellular origin is selected from the group consisting of Tim-3, Her2 and E2 F-1.

14. Use of the cell line according to any one of items 1 to 13 for producing infectious viral particles.

15. A method for producing infectious viral particles comprising the steps of:

(i) growing the cells of the cell line of item 12 or 13 in vitro in the presence or absence of tetracycline or a tetracycline analog; or (ii) infecting the cells of the cell line of any of items 1 to 11 with a viral vector, preferably an adenoviral vector; and (iii) recovering the viral particles.

EXAMPLES

Example 1: Generation of a Stable Clone Expressing TetR

HEK 293 cells were cultivated in DMEM, 10% fetal bovine serum and expanded. At passage 30 the cells were plated in a T-75 cell culture flask and transfected with 24 μg of plasmid pneo/CAG-TetR digested with BsaXI. Pneo/CAG-TetR contains the expression cassette for the Tetracycline repressor and G418-resistance gene (FIG. 1). 48 hours post-transfection, HEK 293 cells were diluted to 1:80 ratio in complete DMEM supplemented with 0.8 mg/ml of G-418. Single, isolated clones resistant to G-418 were picked using standard procedures and transferred in 24-well plates. Each 24-well plate was used to generate 3 plates: 2 of them were used for the screening of single clones, the third was maintained as "master plate". All clones were transduced with ChAdE TetOSeap in duplicate in presence or absence of 1 μg/ml of tetracycline. 48 hours post-infection the supernatant was evaluated for secreted alkaline phosphatase expression by using a chemiluminescence assay (Phospha-Light kit, Applied Biosystems, Foster City, Calif.) according to manufacturer instruction. Clones were ranked by calculating the ratio of SEAP expression in presence/absence of tetracycline. The value represents a measure of the stringency of the transcriptional control: the higher is the value the more stringent is the transcriptional control. Best clones were also evaluated for productivity of adenoviral vectors. M9 clone resulted to be very efficient in controlling expression via tetracycline repressor as well as supporting high levels of adenoviral vectors production.

Example 2: Evaluation of TetR Regulation by SeAp Assay—Comparison of Clone M9 and M38

Clones M9 and M38 were seeded in triplicate in T25 flasks. When the cell monolayers reached 80-90% of confluence (about 3E+06 cells/flask) were infected as follows. The conditioned medium was aspirated and substituted with 5 ml of fresh medium. Cells were then infected with ChAdE TetOSeap using a multiplicity of infection (moi) of 30 particles/cell (vp/cell) in presence or in absence of tetracycline (1 μg/ml). SeAp expression was evaluated two days after infection by testing 50 μl of supernatant per flask. Supernatants harvested from each flask were transferred in a well of a 96-well plate (50 μl/well) to be tested for alkaline phosphatase activity by a chemiluminescent assay (Phospha-Light kit, Applied Biosystems, Foster City, Calif.) according to the manufacturer's instructions. The signal was acquired by using Envision 2012 Multilabel reader (Perkin Elmer). Efficiency of transcriptional control was evaluated by calculating the ratio of SeAp expression value obtained in presence and absence of tetracycline as reported in FIG. 2. The SeAp expression in presence of tetracycline (Tet) is comparable in the two clones indicating that in absence of transcriptional control the HCMV promoter is fully active in M9 as well as in M38 cells. On the contrary, when Tet is not present in the medium and TetR is active and bound to the promoter, the SeAP activity is about 5-fold lower in M9 clone indicating a stronger repression of the HCMV promoter in comparison to M38.

Example 3: Evaluation of Adenovector Productivity in M9 and M38 Cells

M9 and M38 clones were seeded in duplicate in T25 flasks. When cells reached 80-90% confluence were infected with AdTetOE1/F78E2p7 using a moi of 100 vp/cell. AdTetOE1/F78E2p7 is an adenoviral vector carrying a gene that is toxic when expressed in HEK293 cells and therefore it can't be propagated without transcriptional control. HEK 293 cells were infected in parallel as control. When a full cytopathic effect was visible by microscopy (4 days post-infection), cell and medium was harvested from each flask and frozen at −80° C. The viral vector was released from infected cells by three cycles of freeze/thaw (−80° C./37° C.). Then, cell lysates were clarified by centrifugation. Clarified supernatants were analysed by droplet digital polymerase chain reaction employing TaqMan reporter-quencher dye chemistry (Biorad QX200 AutoDG Droplet Digital PCR System) with primers designed to amplify a specific target region of the Human Cytomegalovirus promoter (HCMVp) present in the Adenovector genome and with a dual-labeled fluorescent probe (FAM-TAMRA). The virus yield was evaluated in the crude lysate and expressed as specific productivity in vp/cell. The results (FIG. 3) showed that clones M9 has higher productivity in comparison to M38 and that parental HEK293 cells are not able to support the production of an adenovector expressing a toxic gene. The higher productivity showed by M9 cells is consistent with the results shown in FIG. 2 demonstrating a better transcriptional control of M9 in comparison to M38. Furthermore, HEK293 cells are not able to support the replication of adenoviral vector expressing a toxic gene.

Example 4: TetR Protein Expression in M9 and M38 Cells

The production of TetR in clones M9 and M38 was evaluated by western blot using cell lysate. Cellular proteins were extracted from the M9 and M38 clones and quantified by using Bio-Rad Protein Assay with a standard curve made with bovine serum albumin (BSA). 45 μg of protein extract were denatured at 100° C. in presence of loading buffer containing SDS and loaded on a 4-12% Bis-Tris NuPAGE® gel. After the electrophoresis, the proteins were transferred to nitrocellulose membrane and incubated with TetR monoclonal antibody (Clontech, cat. n° 631131) diluted 1:1000. The signal was revealed by incubating the membrane with anti-mouse secondary antibody conjugated with HRP (SIGMA, cat A9044) diluted 1:3000. As shown in FIG. 4, the expression of TetR was higher in M9 than in M38 cells.

Example 5: Efficiency of Rescue of ChAd Vectors in M9 Cells

In order to further evaluate the efficiency of M9 cells in supporting adenoviral vector production, we have tested for the efficiency of rescue of Species C and E adenoviral vectors by DNA transfection (ChAdN13 TPA4-T1Poly—FIG. 5A and ChAdE egfp—FIG. 5B) in comparison to parental HEK293. M9 and HEK293 cells were cultivated in T25 flask to be transfected in parallel with 10 µg of preAd plasmid DNA by using Lipofectamine® 2000 (Thermo Fisher Scientific cat. N° 11668-019) according to the manufacturer's instructions. The adenoviral vector rescue and amplification was evaluated by QPCR on cell lysates 12 days post-transfection. The primers used in the assay were designed to amplify a specific target region of the Human Cytomegalovirus (HCMV) promoter, and a dual-labeled fluorescent probe (FAM-TAMRA) hybridizes within the amplicon. The results are shown in FIG. 5 and demonstrate a higher efficiency of adenoviral vector production in M9 cells upon transfection for both species C and species E adenoviral vectors.

Example 6: Productivity of ChAd C-Venus and ChAd E-EGFP Vectors

The productivity of two different chimpanzee Ad vectors carrying reporter genes—ChAdC-Venus (FIG. 6A) and ChAdE-EGFP (FIG. 6B) was evaluated in M9 cells in comparison to parental HEK 293 and 293T cells. Monolayers of cells in T25 flask were infected using the same multiplicity of infection for both ChAds. The cells were harvested 72 hours post-infection, when a full cytopathic effect was evident. The vectors were released from infected cells by three cycles of freeze/thaw (−80° C./37° C.). Then cell lysates were clarified by centrifugation and the vector titer was evaluated by Real Time QPCR in the clarified cell lysate. Primers used were designed to amplify a specific target region of the Human Cytomegalovirus (HCMV) present in the Adeno genome. A dual-labeled fluorescent probe (FAM-TAMRA) hybridizes within the amplicon. The results are shown in FIG. 6.

Example 7: Evaluation of the Homogeneity of Transcriptional Control in M9 and T-Rex Cells—Venus Reporter Gene Expression at the Single Cell Level by FACS Analysis The homogeneity of the transcriptional control in the cell line is an important characteristic of a cell line designed to control expression through the adenoviral vector production process. A heterogeneous expression at the single cell level in the cell line used for the production may lead to the selection of rearranged species of vector in the subpopulation of cells that do not repress transcription efficiently. The homogeneity of transcriptional control was evaluated in M9 cell in comparison to commercially available T-Rex cells expressing Tet-R (Invitrogen, lot n° 1804535). Cells were seeded in T25 flasks and infected with ChAdC-Venus using a moi=100 vp/cell. Two days post-infection, cells were detached from flasks and washed with PBS 1× and recovered by centrifugation. Cellular pellet was re-suspended in PBS 1× containing 1% formaldehyde, 2.5 mM EDTA at a final cell density of 1.5E+06 cells/ml. 200 µl of the cell suspension (~3e5 cells in total) were transferred in a well of 96-well plate and analysed by FACS. The results of the FACS analysis reported in FIG. 7 showed that a fluorescence signal is detected in 3.8% of M9 cell line while 26% of T-Rex cells resulted positive. This result demonstrated that M9 cell line is more homogeneous with a higher % of cells (96.2%) that are able to control expression in comparison to T-Rex (74%).

Example 8: ChAd Vector Productivity in M9 and T-Rex Cell Lines

In order to compare the cell-specific and the volumetric productivity of adenoviral vectors in M9 cells in comparison to T-REX cells (Invitrogen, lot n° 1804535), the cell lines were seeded in T25 flasks. Near to confluence cell monolayers were infected with ChAdC-Venus using a moi of 100 vp/cell. Cells were harvested when full CPE was evident by microscopy observation (7 days post-infection). The vector productivity was then determined by Real Time QPCR with primers designed on sequence of HCMV promoter and a dual-labeled fluorescent probe (FAM-TAMRA) hybridizes within the amplicon. The results in FIG. 8 showed a higher productivity of ChAdC-Venus in M9 cells than in T-Rex.

Example 9: TetR Expression Analysis in HCMV-TetR and M9 Cells by Western Blotting 3E+06 cells of each sample (see FIG. 10) were lysed by resuspending the cell pellet in 20 mM TRIS-HCl pH 7.4, 150 mM NaCl, 1 mM EDTA pH 8.0, 10% Triton-X, Protease Inhibitor cocktail Roche cat. 11697498001 for 30 min at 4° C. After incubation, the samples were centrifuged at 4° C. for 30 min at 14000 rpm for clarification. Total protein concentration was evaluated by Bio-Rad protein assay by following the manufacturer instruction and then analyzed by western blotting. 45 ug of protein extract were separated on 4-12% SDS-PAGE under reducing conditions and then transferred onto nitrocellulose membrane by Dry Blot (iBlot Gel Transfer system, Invitrogen). After protein transfer, the membrane was treated with the blocking buffer (Milk 5% in PBS-Tween 0.1%) for 1 hour at room temperature and incubated for 12 hours at +4° C. with the anti-TetR monoclonal antibody (clone 9G9—Clontech Cat. N. #631132) diluted 1:1000. The day after, the membrane was incubated with HRP-conjugated rabbit anti-mouse IgG (SIGMA, cat. n. A9044) for 1 hour at room temperature and then visualized with the Pierce ECL Western blotting substrate (Thermo Scientific, Rockford, Ill.), according to the manufacturer protocol. Anti-tubulin antibody was used as control and to normalize the results. The results shown in FIG. 10 demonstrates that the expression of TetR driven by HCMV promoter declines over time and indicated by the comparison between the samples HEK293 p40—hCMV TetR and HEK293 p60—hCMV TetR showing a strong reduction of the TetR signal. In contrast, the expression of TetR driven by CAG promoter did not decline over time.

Example 10: Reactivation of TetR Expression by Exposing the HEK293 p60—hCMV TetR Cell to Histone Deacetylase (HDAC) Inhibitor To explore the mechanism of HCMV silencing the HEK293 hCMV TetR cells at passage 60 were cultivated in presence of a HDAC inhibitor. The cell culture medium was supplemented with 200 nM of belinostat (PXD101) and then harvested at different time point as indicated in FIG. 11. The TetR expression was evaluated by western blot as indicated in the previous example. The results clearly show that the TetR expression can be reactivated with belinostat but the effect on the expression is only transient. Such a reactivation is not suitable for practical purposes since belinostate is toxic to cells after a more extended exposure.

The inventors assume based on this experiment that hCMV-IE (viral promoter) is prone to transcriptional silencing which is associated with DNA methylation. In contrast, the TetR expression driven by CAG promoter (the most preferred partly cellular promoter of the invention) is stable over cell passaging. The inventors believe that this surprising finding is due to the cells being more prone to silencing viral promoters than cellular or partly cellular promoters.

The invention claimed is:

1. A cell line, wherein the cells of the cell line are HEK293 cells, and wherein a tetracycline repressor (Tet-R) is expressed under the control of a CAG promoter, wherein said cell line is the cell line deposited under accession number 17080901 with the ECACC.

2. The cell line according to claim 1, wherein the expression is stable over time.

3. The cell line according to claim 1, wherein the Tet-R represses transcription of genes comprising in their promoters one or more Tetracycline Operators (TetOs) in the absence of tetracycline or a tetracycline analog.

4. The cell line according to claim 1, wherein the gene encoding Tet-R is codon optimized for expression in eukaryotic cells.

5. The cell line according to claim 1, further comprising
  (i) in its genome a mutation, deletion or insertion that reduces or prevents expression of a functional protein selected from the group consisting of one or more stimulator of an IFN gene, one or more JAK/STAT activator of transcription and one or more IFN-stimulated gene (ISG), and/or
  (ii) a gene encoding a selection marker in genetic linkage to the gene encoding Tet-R.

6. The cell line according to claim 1, comprising stably integrated into its genome a gene encoding tetracycline repressor (Tet-R).

7. The cell line according to claim 1, wherein the cells of the cell line express at least one viral gene that is required for the formation of infectious virus particles.

8. The cell line according to claim 7, wherein the at least one viral gene is selected from the group consisting of E1-A and E1-B.

9. The cell line according to claim 1, further comprising a viral genome capable of assembling into an infectious viral particle and comprising at least one heterologous gene under the control of a promoter comprising one or more Tetracycline Operators (TetO).

10. The cell line according to claim 9, wherein the at least one heterologous gene is selected from the group consisting of self antigens, viral genes, genes of cellular origin, synthetic strings encoding for combination of tumor-associated neo-antigens and strings encoding for neo-epitopes.

11. The cell line according to claim 9, wherein the viral genome is selected from the group consisting of a herpes virus genome, a modified vaccinia Ankara genome and an adenoviral genome.

12. The cell line according to claim 9, wherein the at least one heterologous gene is toxic to the cell or interferes with the viral replication cycle.

13. A method for producing infectious viral particles comprising the steps of:
  (i) growing the cells of the cell line of claim 9 in vitro in the absence of tetracycline or a tetracycline analog; and
  (ii) recovering the viral particles.

* * * * *